US012661258B2

(12) United States Patent
Yin

(10) Patent No.: US 12,661,258 B2
(45) Date of Patent: Jun. 23, 2026

(54) ERGONOMICALLY ADAPTIVE ADJUSTMENT HOT COMPRESS NURSING INSTRUMENT

(71) Applicant: Weiqiang Yin, Beiliu (CN)

(72) Inventor: Weiqiang Yin, Beiliu (CN)

( * ) Notice: Subject to any disclaimer, the term of this patent is extended or adjusted under 35 U.S.C. 154(b) by 583 days.

(21) Appl. No.: 18/304,102

(22) Filed: Apr. 20, 2023

(65) Prior Publication Data

US 2024/0350302 A1     Oct. 24, 2024

(51) Int. Cl.
*A61F 7/02* (2006.01)
*A61F 7/00* (2006.01)
*A61H 23/02* (2006.01)

(52) U.S. Cl.
CPC .............. *A61F 7/02* (2013.01); *A61H 23/02* (2013.01); *A61F 2007/0022* (2013.01); *A61F 2007/0071* (2013.01); *A61F 2007/0093* (2013.01); *A61F 2007/0228* (2013.01); *A61F 2007/0246* (2013.01); *A61F 2007/0282* (2013.01); *A61H 2201/0207* (2013.01); *A61H 2201/1645* (2013.01); *A61H 2201/5015* (2013.01); *A61H 2201/5025* (2013.01); *A61H 2205/083* (2013.01)

(58) Field of Classification Search
CPC .. A61F 7/02; A61F 7/0241; A61F 2007/0022; A61F 2007/0071; A61F 2007/0093; A61F 2007/0225–0228; A61F 2007/0231; A61F 2007/0244–0253; A61F 2007/0282; A61F 2007/0295; A61H 23/02; A61H 23/0254–0263; A61H 2023/0272–0281;

A61H 2201/02; A61H 2201/0207; A61H 2201/0228; A61H 2201/1645–1652; A61H 2201/1654; A61H 2201/5015; A61H 2201/5025; A61H 2201/5035; A61H 2201/5082; A61H 2205/083
See application file for complete search history.

(56) References Cited

U.S. PATENT DOCUMENTS

| | | | | |
|---|---|---|---|---|
| 3,710,784 A | * | 1/1973 | Taylor | A61H 23/0263 601/18 |
| 2005/0090882 A1 | | 4/2005 | Wei | |
| 2006/0200052 A1 | * | 9/2006 | Lin | A61H 23/0263 601/37 |
| 2008/0045910 A1 | | 2/2008 | Chau | |
| 2008/0188911 A1 | | 8/2008 | Chao | |
| 2010/0010599 A1 | * | 1/2010 | Chen | A61F 7/02 607/114 |
| 2013/0237983 A1 | * | 9/2013 | Giles | H05B 1/025 606/41 |
| 2017/0139235 A1 | * | 5/2017 | Liu | A61F 7/007 |
| 2021/0015659 A1 | * | 1/2021 | Lau | A61F 9/04 |
| 2023/0084903 A1 | * | 3/2023 | Marton | A61F 7/007 601/18 |
| 2024/0390181 A1 | * | 11/2024 | Weiss | A47G 9/0223 |

* cited by examiner

*Primary Examiner* — Rachel T Sippel
(74) *Attorney, Agent, or Firm* — Hemisphere Law, PLLC

(57) ABSTRACT

The present disclosure discloses an ergonomically adaptive adjustment hot compress nursing instrument. A storage battery is used to supply electric energy to a heater, so that the heater can generate heat for long time. Real-time constant temperature monitoring and regulation are achieved by combining a temperature sensor and a constant temperature control circuit, which ensures a constant temperature state in a use process, thereby improving a hot compress physiotherapy effect.

6 Claims, 8 Drawing Sheets

181

18

ERGONOMICALLY ADAPTIVE ADJUSTMENT HOT COMPRESS NURSING INSTRUMENT

TECHNICAL FIELD

The present disclosure relates to the technical field of hot compress physiotherapy devices, specifically to an ergonomically adaptive adjustment hot compress nursing instrument.

BACKGROUND

Hot compress has effects of expanding blood vessels, improving local blood circulation and promoting local metabolism, and is beneficial to recovery of diseases. Hot compress itself can also alleviate muscle spasms, relieve pain, reduce swelling, and promote the absorption of inflammation and blood stasis. Medicated hot compress can also make drugs locally absorbed and directly reach diseased sites, making treatment more direct and effective.

In traditional Chinese medicine, there is a saying that infertility is caused by uterine cold. The uterus of a woman is like a warm room for a fetus. If it is cold inside the uterus, a fetus cannot grow up. The "uterus" in traditional Chinese medicine refers not only to the "house" where a baby grows, but also to various organs including the uterus, the ovaries and appendages, and their functions. In order to prevent uterine cold, women should pay special attention to keeping their lower abdomens warm. Especially women working in air-conditioned environments, as well as those who often sit still, should pay more attention to keeping their lower abdomens and lower bodies warm.

Hot compress physiotherapy in an area corresponding to the abdominal uterus of a women can regulate menstruation, nourish blood, warm the uterus, play anti-inflammatory and repair roles, scientifically regulate the uterine environment and effectively protect the physical health and fertility, and is particularly suitable for uterine injury after abortion, gynecological inflammation, infertility due to uterine cold, and dysmenorrhea caused by uterine cold in unmarried women with cold constitutions.

Traditionally, people place heating media such as hot towels and hot water bagsat positions corresponding to the abdominal uteruses of women for hot compress physiotherapy. However, these media cannot maintain heat for a long time and can hardly achieve a constant temperature effect, so they are not ideal for use. With the continuous optimization of electronic sciences and technologies, electronic devices that can provide a heating function have also emerged in the market in recent years. However, most of these products have simple functions and have unreasonable structural design. During use, these products are also unable to achieve a good constant temperature effect and a good close-abutment effect on human body, resulting in unsatisfactory actual use effects.

SUMMARY

The present disclosure aims to provide an ergonomically adaptive adjustment hot compress nursing instrument. A storage battery is used to supply electric energy to a heater, so that the heater can generate heat for long time. Real-time constant temperature monitoring and regulation are achieved by combining a temperature sensor and a constant temperature control circuit, which ensures a constant temperature state in a use process, thereby improving a hot compress physiotherapy effect. A soft elastic pad, a soft heater and a soft heat conduction cover are arranged between a heating body and a human body abutting surface. Mutual cooperation of the soft elastic pad, the soft heater and the soft heat conduction hood can achieve adaptive adjustment for a hot compress working surface and the abdomen of a user. The ergonomically adaptive adjustment hot compress nursing instrument can be suitable for being used by people with different figures, and has a better effect of abutting against the abdomen of the user, which avoids a phenomenon that the physiotherapy effect is reduced by loss of heat caused by untight abutment. The problems mentioned in the background are solved.

In order to achieve the above objective, the present disclosure provides the following technical solution: An ergonomically adaptive adjustment hot compress nursing instrument includes a heating body; two sides of the heating body are butted with two ends of a tie band; the heating body is worn at the abdomen of a user through the tie band to perform hot compress physiotherapy on the uterus of the user; the heating body includes a shell; one side of the shell facing the user is configured as a cambered surface matching the contour of the abdomen; a soft elastic pad, a heater and a soft heat conduction cover are stuck in sequence on one side of the cambered surface facing the user; the soft heat conduction cover is connected with the heater in a heat conduction manner; the soft elastic pad adaptively pushes the heater to collide with the soft heat conduction cover, and makes the heater deform to keep a largest-area contact between the heater and the soft heat conduction cover; and the soft elastic pad self-adapts to deformation of the soft heat conduction cover, so that the soft heat conduction cover adaptively keeps a good abutment against the contours of different types of abdomens.

Preferably, the soft elastic pad is a sponge sheet; one side of the sponge sheet facing the heating body abuts against the cambered surface, and the other side abuts against the heater; and the heater is a soft sheet.

Preferably, the heater includes a thin-sheet encapsulation film; an intestinal tract-shaped copper heater is arranged on the encapsulation film, and a temperature sensor is encapsulated; and the temperature sensor is conductively connected with the soft heat conduction cover.

Preferably, the soft heat conduction cover is a cover made of a nylon fabric; and a circumferential edge of the soft heat conduction cover is fixedly connected to a circumferential edge of the heating body, so that the soft heat conduction cover is formed into a cambered surface shape close to the form of the cambered surface.

Preferably, the heating body includes a shell; the shell includes a front shell, an inner shell and a rear shell; an accommodating cavity is formed between the front shell and the inner shell; a circuit board component is arranged in the accommodating cavity; the rear shell is detachably connected to one side of the inner shell away from the front shell; and the cambered surface is formed on one side of the rear shell away from the inner shell.

Preferably, a storage battery and a vibration motor are arranged in the accommodating cavity; both the storage battery and the vibration motor are electrically connected with the circuit board component; the circuit board component is electrically connected with a control button and a USB interface; a button through hole is formed in a front end of the front shell; a button panel is mounted in the button through hole; the button panel is connected with the control button in a pressing manner; and the USB interface is arranged in a through hole pre-formed in the inner shell and extends out from the through hole.

Preferably, the vibration motor is centered at a central axis of the inner shell.

Preferably, a plurality of clasping positions penetrating through the shell are arranged on the inner shell; the rear shell is provided with clasps which correspond to the clasping positions and extend out of a surface of the shell; and the rear shell achieves detachable connection by the clasping action between the clasps and the clasping positions.

Compared with the prior art, the present disclosure has the beneficial effects:

According to the present disclosure, a storage battery is used to supply electric energy to a heater, so that the heater can generate heat for long time. Real-time constant temperature monitoring and regulation are achieved by combining a temperature sensor and a constant temperature control circuit, which ensures a constant temperature state in a use process, thereby improving a hot compress physiotherapy effect. A soft elastic pad, a soft heater and a soft heat conduction cover are arranged between a heating body and a human body abutting surface. Mutual cooperation of the soft elastic pad, the soft heater and the soft heat conduction hood can achieve adaptive adjustment for a hot compress working surface and the abdomen of a user. The ergonomically adaptive adjustment hot compress nursing instrument can be suitable for being used by people with different figures, and has a better effect of abutting against the abdomen of the user, which avoids a phenomenon that the physiotherapy effect is reduced by loss of heat caused by untight abutment.

BRIEF DESCRIPTION OF THE DRAWINGS

FIGS. 6(a)-6 (c) are schematic diagrams of a control circuit of the present disclosure;

Figure 1:
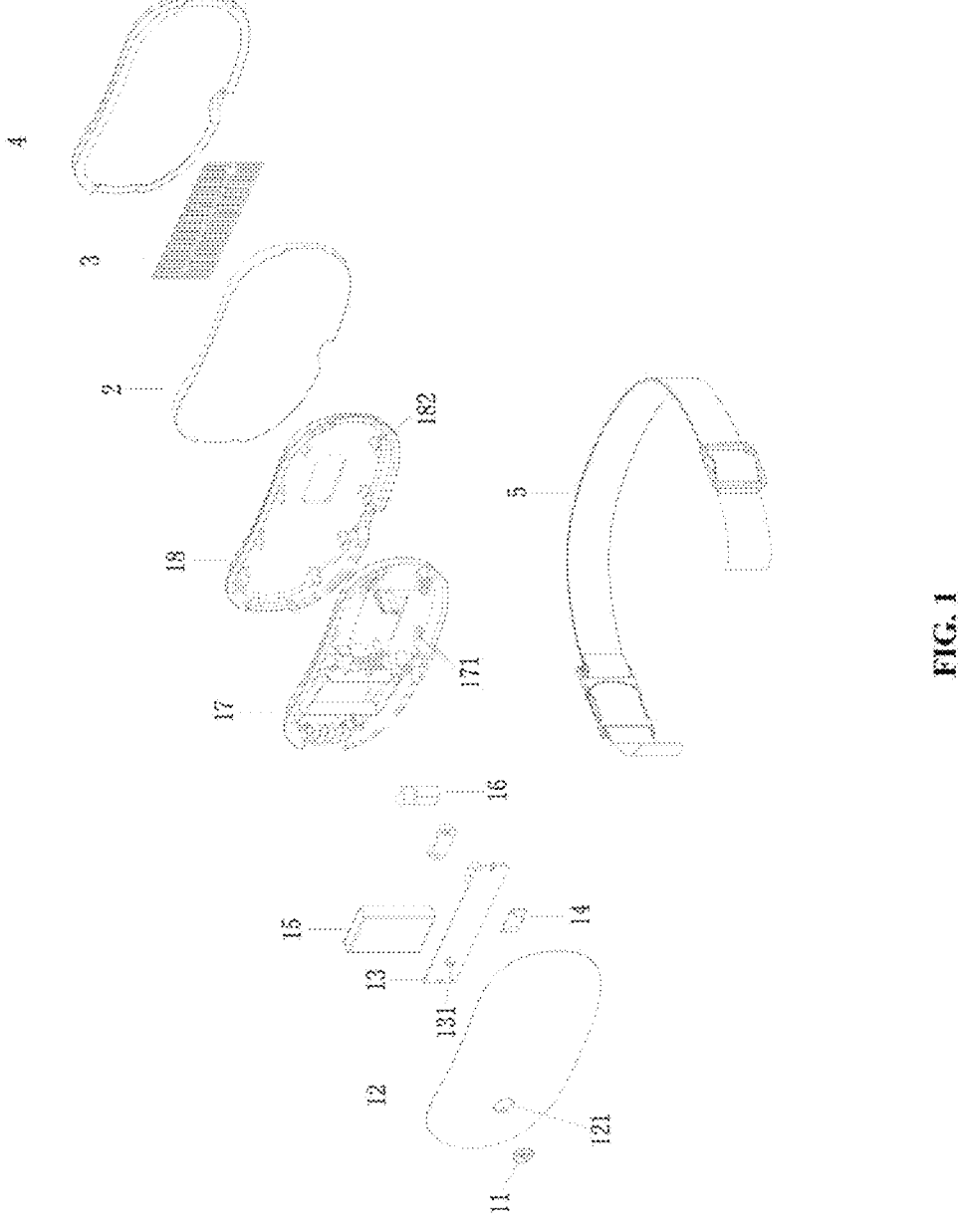
FIG. 1 is a structural exploded diagram I of the present disclosure.
Figure 2:
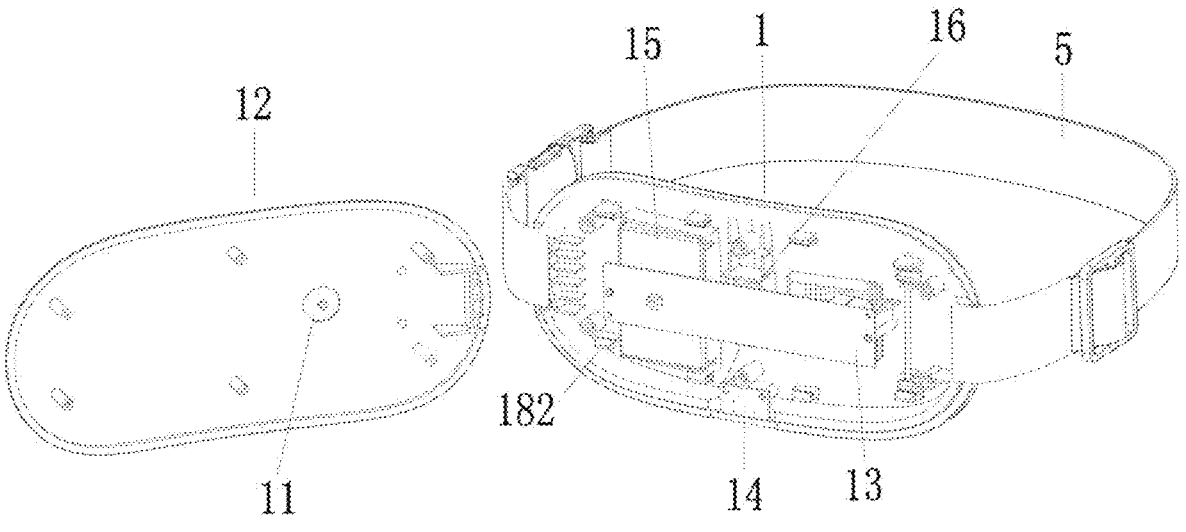
FIG. 2 is a structural exploded diagram II of the present disclosure.
Figure 3:
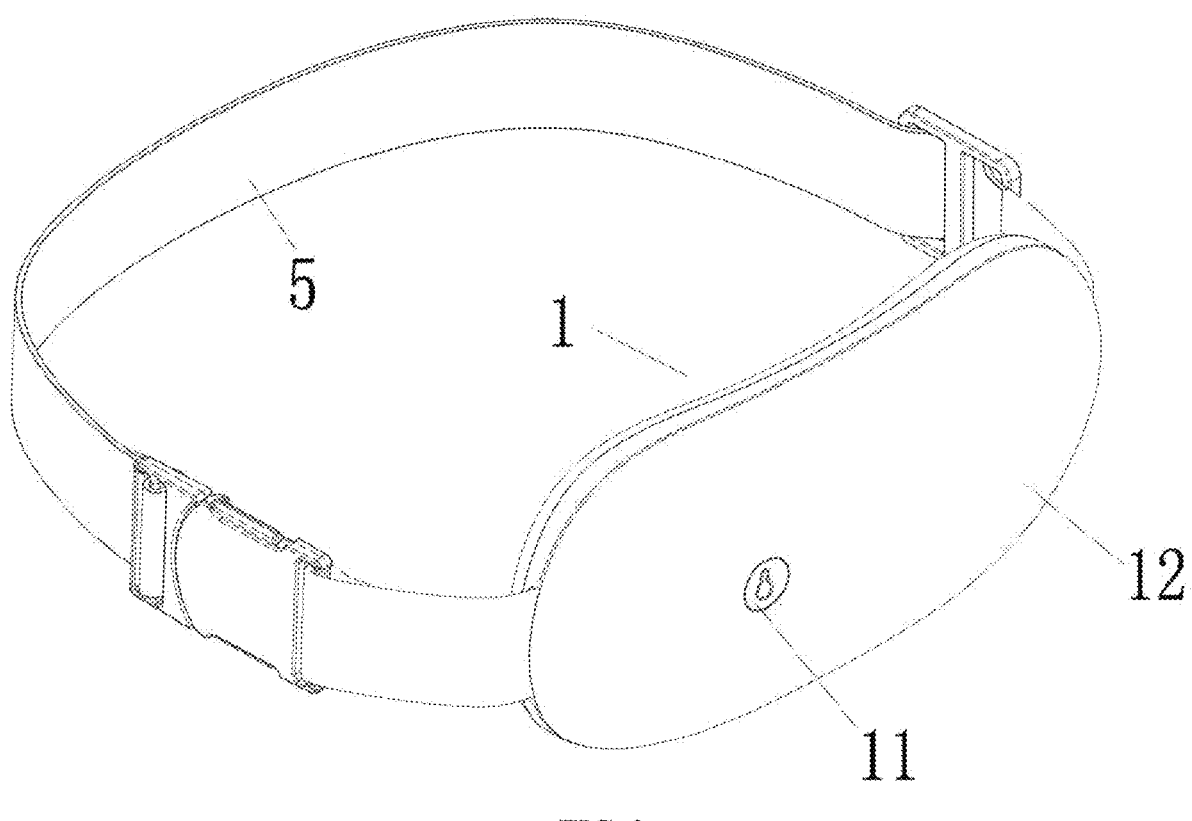
FIG. 3 is a reference diagram I of a use state of the present disclosure.
Figure 4:
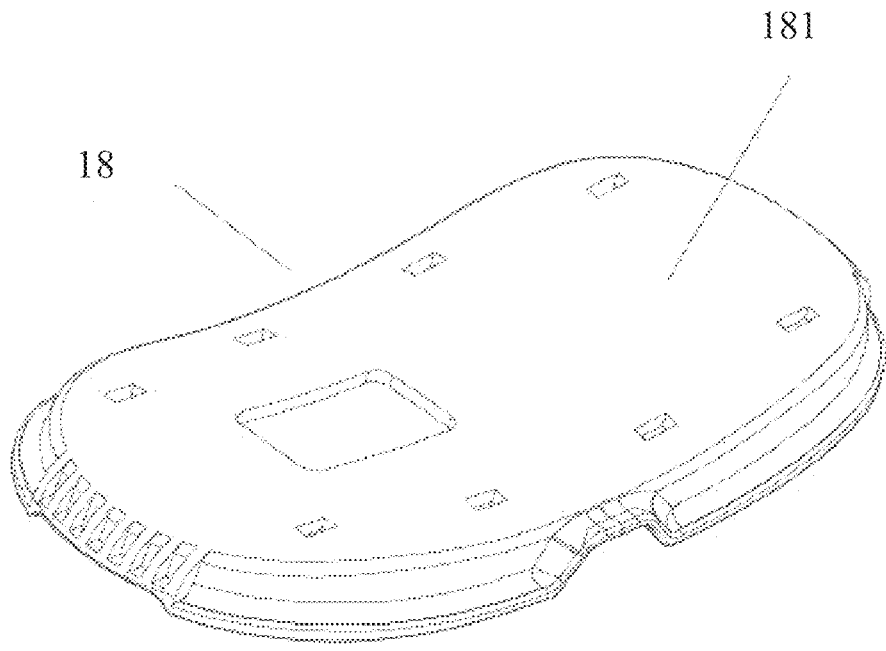
FIG. 4 is a schematic structural diagram of a rear shell of the present disclosure.
Figure 5:
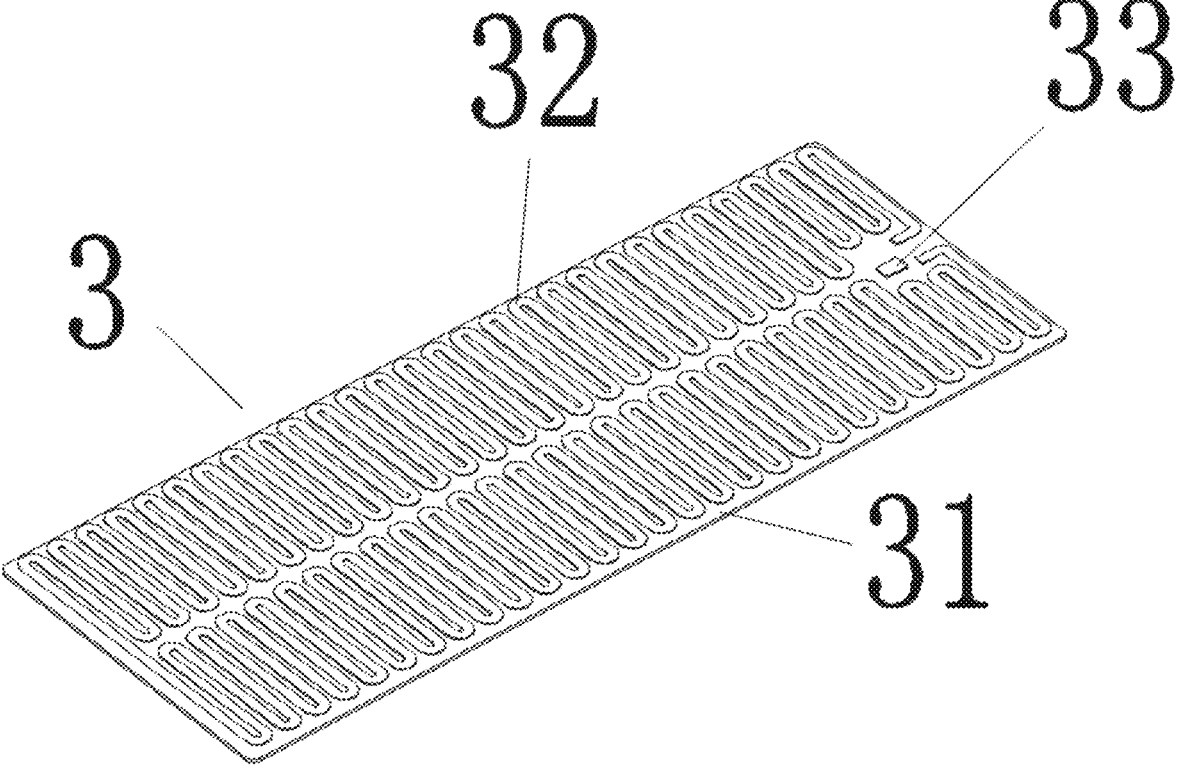
FIG. 5 is a schematic structural diagram of a heater of the present disclosure.

In the drawings: 1: heating body; 11: button panel; 12: front shell; 13: circuit board component; 131: control button; 14: USB interface; 15: storage battery; 16: vibration motor; 17: inner shell; 171: clasping position; 18: rear shell; 181: cambered surface; 182: clasp; 2: soft elastic pad; 3: heater; 31: encapsulation film; 32: copper heater; 33: temperature sensor; 4: soft heat conduction cover; and 5: tie band.

DETAILED DESCRIPTION OF THE EMBODIMENTS

The technical solutions in the embodiments of the present disclosure will be described clearly and completely below with reference to the drawings in the embodiments of the present disclosure. Obviously, the embodiments described herein are only part of the embodiments of the present disclosure, not all the embodiments. Based on the embodiments in the present disclosure, all other embodiments obtained by those of ordinary skill in the art without creative work shall fall within the protection scope of the present disclosure.

Referring to FIG. 1 to FIG. 5, an ergonomically adaptive adjustment hot compress nursing instrument includes a heating body 1. Two sides of the heating body 1 are butted with two ends of a tie band 5. The heating body is worn at the abdomen of a user through the tie band 5 to perform hot compress physiotherapy on the uterus of the user. The heating body 1 includes a shell. One side of the shell facing the user is configured as a cambered surface 181 matching the contour of the abdomen; a soft elastic pad 2, a heater 3 and a soft heat conduction cover 4 are stuck in sequence on one side of the cambered surface 181 facing the user. The soft heat conduction cover 4 is connected with the heater 3 in a heat conduction manner. The soft elastic pad 2 adaptively pushes the heater 3 to collide with the soft heat conduction cover 4, and makes the heater 3 deform to keep a largest-area contact between the heater 3 and the soft heat conduction cover 4. The soft elastic pad 2 self-adapts to deformation of the soft heat conduction cover 4, so that the soft heat conduction cover 4 adaptively keeps a good abutment against the contours of different types of abdomens.

The soft elastic pad 2 is a sponge sheet. One side of the sponge sheet facing the heating body 1 abuts against the cambered surface 181, and the other side abuts against the heater 3. The heater 3 is a soft sheet. The heater 3 includes a thin-sheet encapsulation film 31. An intestinal tract-shaped copper heater 32 is arranged on the encapsulation film 31, and a temperature sensor 33 is encapsulated. The temperature sensor 33 is conductively connected with the soft heat conduction cover 4. The soft heat conduction cover 4 is a cover made of a nylon fabric. A circumferential edge of the soft heat conduction cover 4 is fixedly connected to a circumferential edge of the heating body 1, so that the soft heat conduction cover 4 is formed into a cambered surface shape close to the form of the cambered surface 181.

The heating body 1 includes a shell. The shell includes a front shell 12, an inner shell 17 and a rear shell 18. An accommodating cavity is formed between the front shell 12 and the inner shell 17. A circuit board component 13, a storage battery 15 and a vibration motor 16 are arranged in the accommodating cavity. Both the storage battery 15 and the vibration motor 16 are electrically connected with the circuit board component 13. The circuit board component 13 is electrically connected with a control button 131 and a USB interface 14. A button through hole 121 is formed in a front end of the front shell 12. A button panel 11 is mounted in the button through hole 121. The button panel 11 is connected with the control button 131 in a pressing manner. The USB interface 14 is arranged in a through hole preformed in the inner shell 17 and extends out from the through hole. When connected to an external power supply through a charging cable, the USB interface 14 can charge the storage battery 15 to supplement electric energy. A button corresponding to the button panel 11 is pressed and adjusted to adjust and control working states of the heater 3 and the vibration motor 16. The rear shell 18 is detachably connected to one side of the inner shell 17 away from the front shell 12, and the cambered surface 181 is formed on one side of the rear shell 18 away from the inner shell 17. A plurality of clasping positions 171 penetrating through the shell are arranged on the inner shell 17. The rear shell 18 is provided with clasps 182 which correspond to the clasping positions 171 and extend out of a surface of the shell; and the rear shell 18 achieves detachable connection by the clasping action between the clasps 182 and the clasping positions 171. The vibration motor 16 is centered at a central axis of the inner shell 17. When the vibration motor 16 works, a vibration massage function can be provided while the heating body 1 realizes hot compress, thereby improving the physiotherapy effect.

Figure 6:
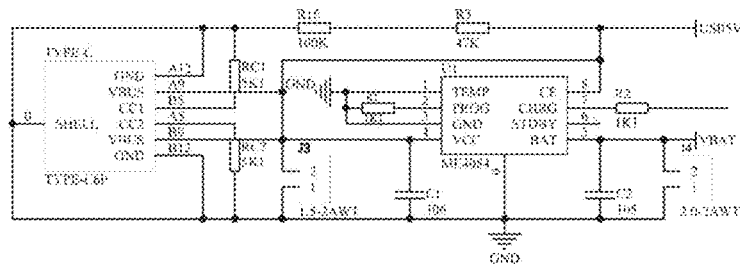
Figure 6:
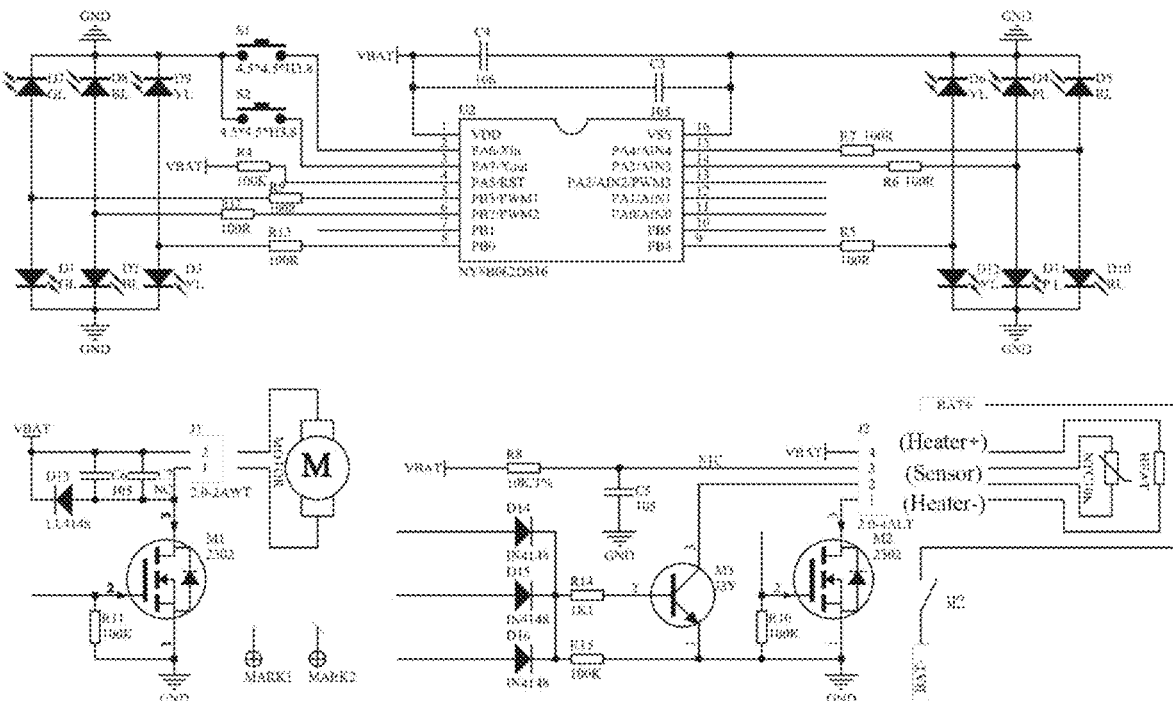
Figure 7:
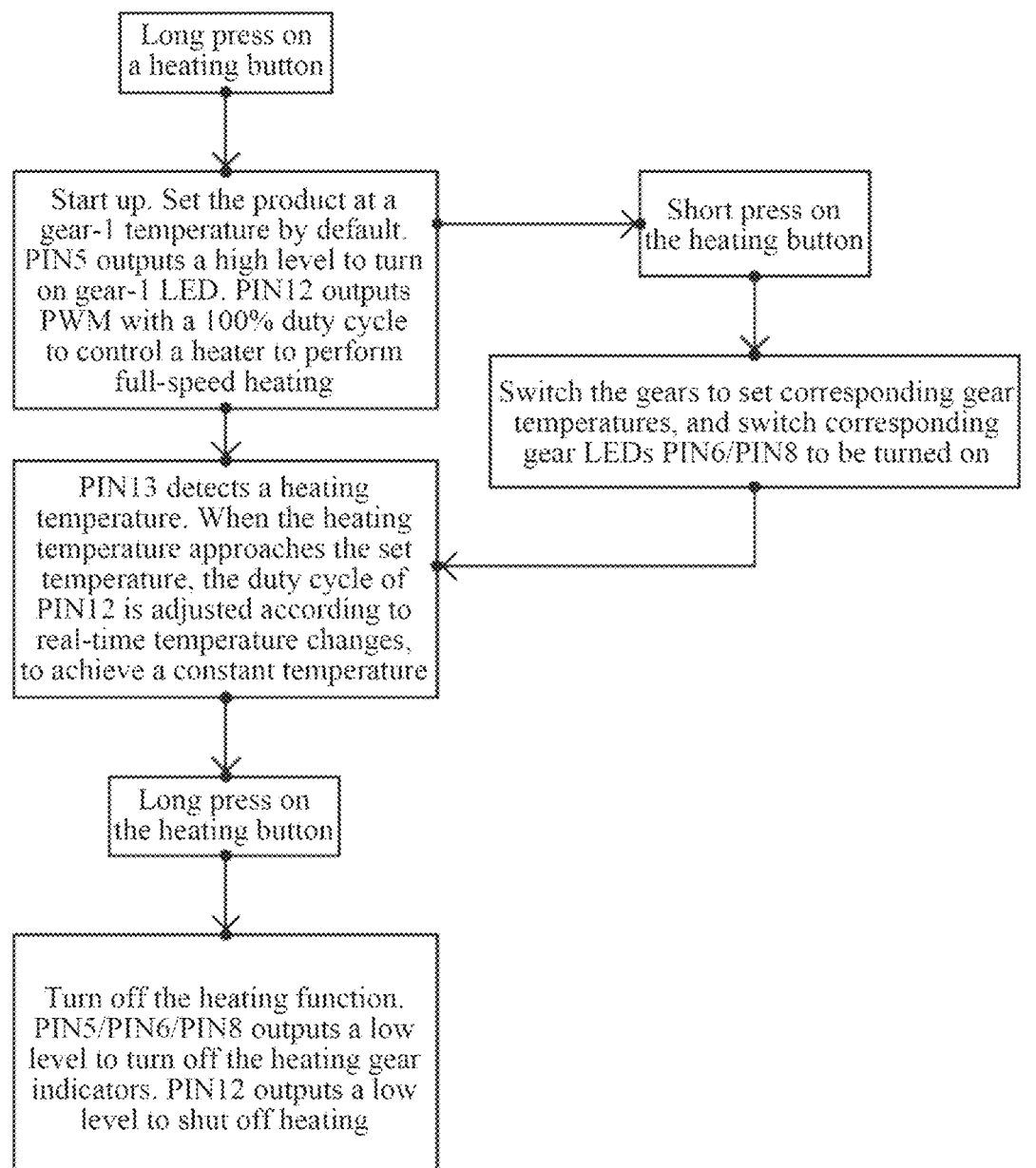
FIG. 7 is a block diagram of a trend of a heating circuit of the present disclosure.
Figure 8:
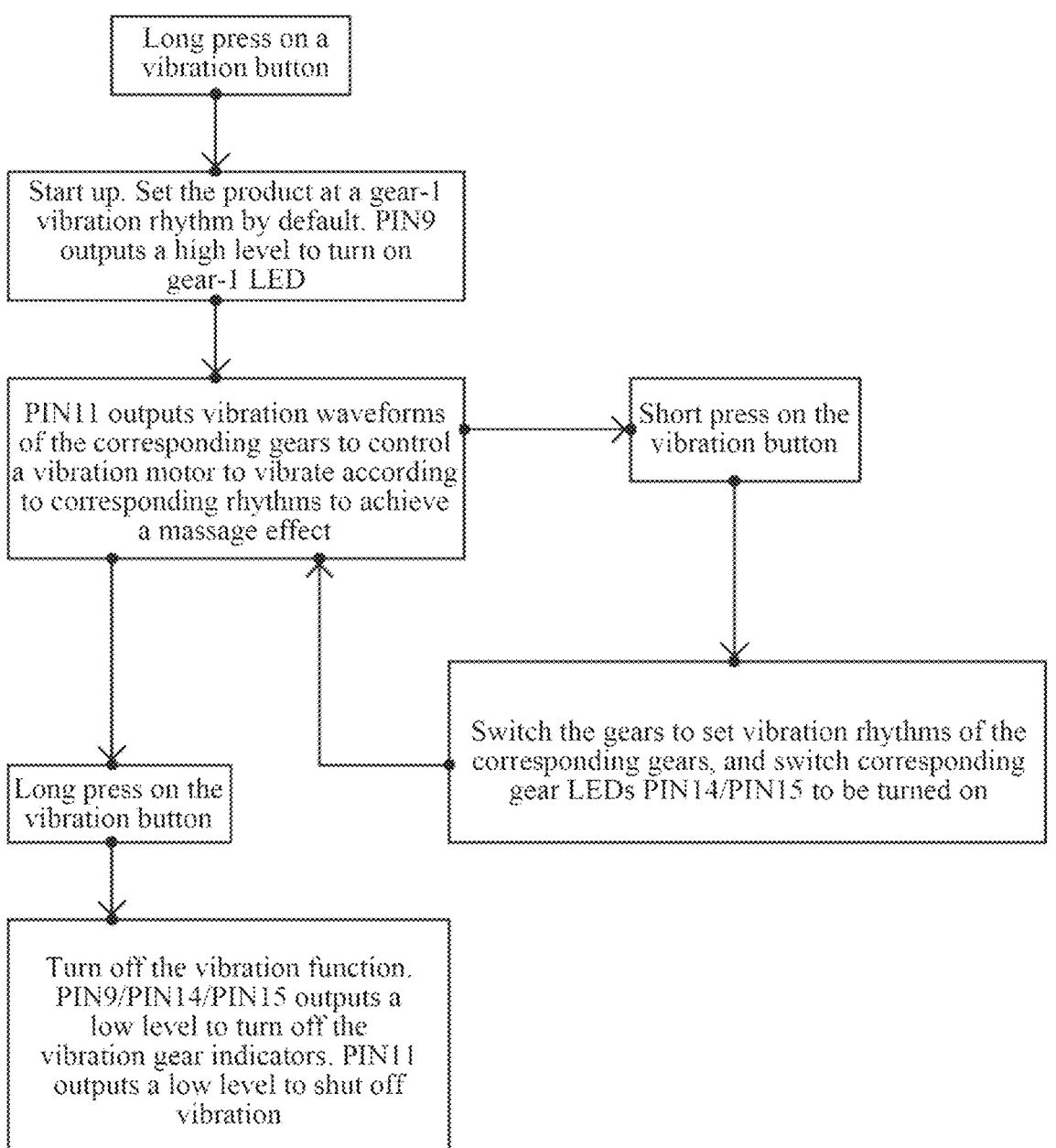
FIG. 8 is a block diagram of a trend of a vibration massage circuit of the present disclosure.

Referring to FIG. 6 to FIG. 8, a charging circuit is described as follows: When a USB cable is plugged to charge a product, a level of (input detection-PIN7) increases. A single-chip microcomputer will be awakened and run a charging indication program if it is in an off state. If the single-chip microcontroller is in a working state, heating and vibration functions are forcedly turned off, the buttons fail, and the single-chip microcontroller is switched to the charging indication program, and a vibration gear-3 LED-PIN15 performs charging state indication. The LED is breathing if the product is not fully charged. The LED is constantly on if the product is fully charged. For charging indication, the single-chip microcontroller determines whether the battery is fully charged by detecting a level of (charging-PIN10), and controls a (heating gear-3 LED-PIN8). When the charging ends and the USB cable is unplugged, the level of (input detection-PIN7) decreases. The single-chip microcomputer exits the charging indication program and is powered off. The buttons are recovered.

For a heating function: a long press on (heating button-PIN3) controls the heating function to be on/off. After startup, a short press can cyclically switch heating temperature gears. After the heating function is turned on, (heating-PIN12) outputs a high level to control an N-MOS transistor M2 to be turned on, so that the heater is powered on and performs full-speed heating. At the same time, (NTC-PIN13) performs ADC detection to obtain a sensor temperature. When the temperature is close to a set temperature of a selected gear, and (heating-PIN12) outputs a PWM square wave.

Furthermore, a PWM duty cycle is adjusted in real time according to the detected temperature, to achieve a constant temperature effect.

For a vibration function: a long press on (vibration button-PIN2) controls the vibration function to be on/off. After startup, a short press can cyclically switch vibration rhythm gears. After the vibration function is turned on, (vibration-PIN11) outputs a preset vibration rhythm square wave of a corresponding gear. An N-MOS transistor M1 is controlled to be rhythmically turned on and turned off, so that the vibration motor rhythmically vibrates and stops, to achieve a vibration massage effect.

A circuit control principle is composed of a lithium battery charging management circuit, a vibration motor drive circuit, a heater drive circuit, a temperature detection circuit, a human-computer interaction circuit, and the like.

A charging circuit is composed of a TYPE-C mother base on a board B, a resistor RC1, a resistor RC2 and a B-A connection line (plugged to a J3 socket), and a J3 socket base on a board A, an ME4084 charging management IC, IC peripheral elements (R1, R2, C1 and C2), a J4 battery holder, a resistor R3, and a resistor R16. The resistor R3 and the resistor R16 are connected in series to the J3 socket, and a midpoint of the serially connected whole is connected to PIN7 of an MCU as input detection (an I/O is set to be in a suspended state to detect whether TYPE-C is made with a 5V input). PIN7 of the ME4084 is connected to PIN10 of the MCU through the resistor R2 to detect a charging state (the I/O is set to be pull-up). A working process of the circuit is as follows: When voltage of 5 V is made to TYPE-C to charge the product, midpoint voltages of the resistors R3 and R16 change from low to high, so that the MCU enters a charging indication state (in which, the vibration and heating functions are not available, and buttons are not available). At the same time, the voltage of 5 V is input to PIN4 and PIN8 of the ME4084 to enable the charging IC to start working. The capacitor C1 is a 5V input filter capacitor, and the capacitor C2 is an ME408 charging output filter capacitor and is connected to a battery cathode. The resistor R1 is used for setting a constant charging current for the ME4084, and the charging state is fed back to PIN10 of the MCU through the resistor R2. After the MCU enters the charging indication state, this state is displayed through a state control indicator light of PIN10. If PIN10 is at a low level, it is indicated that the battery is not fully charged. PIN8 and PIN15 of the MCU output a breathing LED PWM to control the heating 3-gear LED and the vibration 3-gear LED together for breathing LED indication. When PIN10 is at a high level, it is indicated that the battery is fully charged. PIN8 and PIN15 of MCU outputs high levels to control the heating 3-gear LED and the vibration 3-gear LED to be on for long time. When the charging ends and the charging cable is unplugged, the resistors R3 and R16 lose the voltage of 5 V, and only R16 of PIN7 of the MCU is connected to GND, so the high level becomes a low level, causing the MCU to exit the charging indication state. PIN4 and PIN8 of the ME4084 lose power, and the charging IC enters dormancy.

The human-computer interaction circuit is composed of a vibration function button S1; a heating function button S2; a vibration gear indicator, in which gear-1 LEDs D6 and D12 are connected in parallel, gear-2 LEDs D4 and D11 are connected in parallel, and gear-3 LEDs D5 and D10 are connected in parallel; vibration indicator current limiting resistors R5, R6, R7; a heating gear indicator, in which gear-1 LEDs D7 and D1 are connected in parallel, gear-2 LEDs D8 and D2 are connected in parallel, and gear-3 LEDs D9 and D3 are connected in parallel; and heating indicator current limiting resistors R9, R12, and R13. One end of the vibration function button S1 is connected to GND, and one end is connected to PIN2 of the MCU (the I/O is set to pull-up). When the button is pressed, PIN2 is at a low level. When the button is released, PIN2 is at a high level. One end of the heating function button S2 is connected to GND, and one end is connected to PIN3 of the MCU (the I/O is set to pull-up). When the button is pressed, PIN3 is at a low level. When the button is released, PIN3 is at a high level. Negative poles of the vibration gear-1 LEDs D6 and D12 are connected to GND, and positive poles of the vibration gear-1 LEDs are connected in series to R5 and then are connected to PIN9 of the MCU, so that PIN9 of the MCU outputs a high level to turn on the vibration gear-1 LEDs, and outputs a low level to turn off the LEDs. Negative poles of the vibration gear-2 LEDs D4 and D11 are connected to GND, and positive poles of the vibration gear-2 LEDs are connected in series to R6 and then are connected to PIN14 of the MCU, so that PIN14 of the MCU outputs a high level to turn on the vibration gear-2 LEDs, and outputs a low level to turn off the LEDs. Negative poles of the vibration gear-3 LEDs D5 and D10 are connected to GND, and positive poles of the vibration gear-3 LEDs are connected in series to R7 and then are connected to PIN15 of the MCU, so that PIN15 of the MCU outputs a high level to turn on the vibration gear-3 LEDs, and outputs a low level to turn off the LEDs. Negative poles of the heating gear-1 LEDs D7 and D1 are connected to GND, and positive poles of the heating gear-1 LEDs are connected in series to R9 and then are connected to PIN5 of the MCU, so that PIN5 of the MCU outputs a high level to turn on the heating gear-1 LEDs, and outputs a low level to turn off the LEDs. Negative poles of the heating gear-2 LEDs D8 and D2 are connected to GND, and positive poles of the heating gear-2 LEDS are connected in series to R12 and then are connected to PIN6 of the MCU, so that PIN6 of the MCU outputs a high level to turn on the heating gear-2 LEDs, and outputs a low level to turn off the LEDs. Negative poles of the heating gear-3 LEDs D9 and D3 are connected to GND, and positive poles of the heating gear-3 LEDs are connected in series to R13 and then are connected to PIN8 of the MCU, so that PIN8 of the MCU outputs a high level to turn on the heating gear-3 LEDs, and outputs a low level to turn off the LEDs.

The vibration motor drive circuit is composed of a diode D13, a capacitor C6, a capacitor C7, a motor seat J1, an N-MOS transistor M1, and a resistor R11. The diode D13 is connected in reverse parallel to positive and negative poles of the motor to absorb a reverse electromotive force when the motor is turned off, to protect a drive tube. The capacitor C6 is connected in parallel to the positive and negative poles of the motor to assist in motor starting (it is difficult to start the motor under the drive of a vibration square wave). A drain and source of the N-MOS transistor M1 are connected in series to a negative pole loop of the motor, which is equivalent to a switch of the motor. A level at a gate of the N-MOS transistor can control ON/OFF of the MOS transistor, and then control start/stop of the motor. The gate is directly connected to PIN11 of the MCU. The resistor R11 is a pull-down resistor of the gate of the MOS transistor, to provide a normally OFF state for the MOS transistor. A working process of the vibration function is as follows: A long press is made on the vibration function button S1. When the MCU detects that PIN2 has a low level for about 2 s, the vibration function is turned on, which is in a gear-1 vibration mode by default. The corresponding gear indicator is turned on according to the above-mentioned drive manner of the human-computer interaction circuit. PIN11 of the MCU outputs vibration square waves of the gear-1 mode to drive the N-MOS transistor M1 to be turned on and turned off according to a waveform. M1 is turned on at a high level portion of the waveform, and the motor is powered on to work (a current is output from the battery cathode to the positive pole of the vibration motor through PIN2 of the motor seat J1, and then returns to PIN1 of the motor seat J1 from the negative pole of the motor through the motor, and the current is input from the drain of the N-MOS transistor M1 and output from the source, and returns to a battery anode). M1 is turned off at a low level portion of the waveform, and the motor is powered off, so that the vibration motor generates a corresponding vibration rhythm. After the vibration function is turned on, a short press is made on the vibration function button S1 (MCU detects that PIN2 has a transitory low level), and three vibration gear modes can be cyclically switched. The corresponding gear indicators are turned on according to the above-mentioned drive manner of the human-machine interaction circuit. PIN11 of the MCU switches vibration rhythm square waves of the corresponding gears to drive the N-MOS transistor M1 (each gear has a different vibration waveform combination, which is actually a PWM waveform combination with a different duty cycle, reflecting different vibration rhythms). When the vibration function needs to be turned off, a long press is made on the vibration function button S1. When the MCU detects that PIN2 has a low level for about 2 s, the vibration function is turned off. The vibration gear indicators are turned off according to the above-mentioned drive manner of the human-computer interaction circuit, and PIN11 of the MCU outputs a low level to turn off the N-MOS transistor M1, and the motor is powered off to stop working.

The heater drive circuit is composed of a heater component seat J2, an N-MOS transistor M2, a resistor R10, a resistor R8, a capacitor C5, a triode M3, a resistor R14, a resistor R15, and diodes D14, D15, and D16. PIN1 and PIN4 of the seat J2 are connected to an external heater, and PIN2 and PIN3 are connected to an NTC thermistor on a heater component. A drain and source of the N-MOS transistor M2 are connected in series to a negative pole loop of a heater, which is equivalent to a switch of the heater. A level at a gate of the N-MOS transistor can control ON/OFF of the MOS transistor, and then control power on and power off of the heater. The gate is directly connected to PIN12 of the MCU. The resistor R10 is a pull-down resistor of the gate of the MOS transistor, to provide a normally OFF state for the MOS transistor. The resistor R8 is connected in series with the NTC thermistor, and a midpoint of the serially connected whole is connected to PIN13 of the MCU for temperature detection after voltage buffering by the capacitor C5. A lower temperature indicates a higher voltage on the capacitor C5 after voltage division between the resistor R8 and the NTC, and a higher temperature indicates a lower voltage on the capacitor C5 after voltage division between the resistor R8 and the NTC. A corresponding temperature change can be obtained by internal ADC detection of PIN13 of the MCU. The triode M3 is connected in series to a negative pole loop of the NTC thermistor, and a base of the triode is connected to drive PINs of the three heating gear indicators through the resistor R14 and the three diodes. According to the above-mentioned drive manner of the human-computer interaction circuit, as long as one heating gear indicator is turned on, the base of the triode M3 can obtain a high level, and the triode M3 can be turned on, so that the sensor is powered on to work. When the three heating gear indicators are turned off (when the heating function is turned off), the base of the transistor M3 loses power. Under the pull-down action of the resistor R15, the transistor M3 is turned off, causing a current loop of the sensor to be cut off. In this way, static current consumption is reduced when the heating function is not turned on. A working process of the heating function is as follows: A long press is made on the heating function button S2. When the MCU detects that PIN3 has a low level for about 2 s, the heating function is turned on, which is in a gear-1 heating mode by default. The corresponding gear indicator is turned on according to the above-mentioned drive manner of the human-computer interaction circuit. PIN12 of the MCU outputs a high level to drive the N-MOS transistor M2 to be turned on, so that the heater is powered on to start heating (a current is output from the battery cathode to the positive pole of the heater through PIN4 of the heater assembly seat J2, and then returns to PIN1 of the heater assembly seat J2 from the negative pole of the heater through the heater, and the current is input from the drain of the N-MOS transistor M2 and output from the source, and returns to the battery anode). At the same time, PIN13 of the MCU performs temperature detection. When a heating temperature approaches a set temperature of the gear, the output of PIN12 output of the MCU becomes a PWM square wave (M2 is turned on at a high level portion of the waveform, and the heater is powered on; M2 is turned off at a low level portion of the waveform, and the heater is powered off; and the frequency is switched quickly). Constant temperature heating is achieved by increasing or decreasing the PWM duty cycle according to temperature changes, that is, by controlling time proportions of powering on and powering off of the heater. After the heating function is turned on, a short press is made on the heating function button S2 (MCU detects that PIN3 has a transitory low level), and three heating gear modes can be cyclically switched. The corresponding gear indicators are turned on according to the above-mentioned drive manner of the human-machine interaction circuit. A temperature control upper limit of PIN12 of the MCU is switched to set temperature points of the corresponding gears. When the heating function needs to be turned off, a long press is made on the heating function button S2. When the MCU detects that PIN3 has a low level for about 2 s, the heating function is turned off. The heating gear indicators are turned off according to the above-mentioned drive manner of the human-computer interaction circuit (after the heating indicators are turned off, the temperature detection circuit will also be powered off by the triode M3), and PIN12 of the MCU outputs a low level to turn off the N-MOS transistor M2, and the heater is powered off to stop heating.

The heating function and vibration function of this product can be operated independently or simultaneously, which are controlled by the corresponding function buttons. When all the functions of the product are turned off, the MCU will enter a dormancy state to reduce static power consumption. At this time, the level changes of the input detection (PIN7 of the MCU), the vibration function button (PIN2 of the MCU), and the heating function button (PIN3 of the MCU) can wake up the MCU and enter the corresponding working states according to their respective conditions. The MCU has a low power protection function. When the product works to a low battery state, the MCU will turn off all the functions, then provide a low battery prompt (the heating gear-3 LEDs and the vibration gear-3 LEDs flash 10 times before being turned off), and the product is finally powered off.

In summary, according to the present disclosure, a storage battery is used to supply electric energy to a heater, so that the heater can generate heat for long time. Real-time constant temperature monitoring and regulation are achieved by combining a temperature sensor and a constant temperature control circuit, which ensures a constant temperature state in a use process, thereby improving a hot compress physiotherapy effect. A soft elastic pad, a soft heater and a soft heat conduction cover are arranged between a heating body and a human body abutting surface. Mutual cooperation of the soft elastic pad, the soft heater and the soft heat conduction hood can achieve adaptive adjustment for a hot compress working surface and the abdomen of a user. The ergonomically adaptive adjustment hot compress nursing instrument can be suitable for being used by people with different figures, and has a better effect of abutting against the abdomen of the user, which avoids a phenomenon that the physiotherapy effect is reduced by loss of heat caused by untight abutment.

It should be noted that in this context, relational terms such as first and second are used merely to distinguish one entity or operation from another entity or operation, instead of necessarily requiring or implying that these entities or operations have any of these actual relationships or orders. Furthermore, terms "include", "including" or any other variants are meant to cover non-exclusive inclusions, so that a process, method, object or device that includes a series of elements not only includes those elements, but also includes other elements which are not definitely listed, or further includes inherent elements of this process, method, object or device.

Although the embodiments of the present disclosure have been shown and described, it will be understood by those of ordinary skill in the art that various changes, modifications, substitutions, and transformations can be made to these embodiments without departing from the principle and spirit of the present disclosure. The scope of the present disclosure is defined by the attached claims and their equivalents.

What is claimed is:

1. An ergonomically adaptive adjustment hot compress nursing instrument, comprising a heating body (1), wherein two sides of the heating body (1) are butted with two ends of a tie band (5); the heating body is configured to be worn at the abdomen of a user through the tie band (5) to perform hot compress physiotherapy on the uterus of the user; the heating body (1) comprises a shell; one side of the shell configured to face the user is configured as a cambered surface (181) configured to match the contour of the abdomen; a soft elastic pad (2), a heater (3) and a soft heat conduction cover (4) are stuck in sequence on one side of the cambered surface (181) configured to face the user; the soft heat conduction cover (4) is connected with the heater (3) in a heat conduction manner; the soft elastic pad (2) adaptively pushes the heater (3) to collide with the soft heat conduction cover (4), and makes the heater (3) deform to keep a largest-area contact between the heater (3) and the soft heat conduction cover (4); and the soft elastic pad (2) self-adapts to deformation of the soft heat conduction cover (4), so that the soft heat conduction cover (4) is configured to adaptively keep a good abutment against the contours of different types of abdomens;

wherein the heating body (1) comprises a shell; the shell comprises a front shell (12), an inner shell (17) and a rear shell (18); an accommodating cavity is formed between the front shell (12) and the inner shell (17); a circuit board component (13) is arranged in the accommodating cavity; the rear shell (18) is detachably connected to one side of the inner shell (17) away from the front shell (12) and the cambered surface (181) is formed on one side of the rear shell (18) away from the inner shell (17).

2. The ergonomically adaptive adjustment hot compress nursing instrument according to claim 1, wherein the soft elastic pad (2) is a sponge sheet; one side of the sponge sheet facing the heating body (1) abuts against the cambered surface (181), and another side of the sponge sheet abuts against the heater (3); and the heater (3) is a soft sheet.

3. The ergonomically adaptive adjustment hot compress nursing instrument according to claim 1, wherein the heater (3) comprises a thin-sheet encapsulation film (31);

an intestinal tract-shaped copper heater (32) is arranged on the encapsulation film (31), and a temperature sensor (33) is encapsulated; and the temperature sensor (33) is conductively connected with the soft heat conduction cover (4).

4. The ergonomically adaptive adjustment hot compress nursing instrument according to claim 1, wherein the soft heat conduction cover (4) is a cover made of a nylon fabric; and a circumferential edge of the soft heat conduction cover (4) is fixedly connected to a circumferential edge of the heating body (1), so that the soft heat conduction cover (4) is formed into a cambered surface shape close to the form of the cambered surface (181).

5. The ergonomically adaptive adjustment hot compress nursing instrument according to claim 1, wherein a storage battery (15) and a vibration motor (16) are arranged in the accommodating cavity; both the storage battery (15) and the vibration motor (16) are electrically connected with the circuit board component (13); the circuit board component (13) is electrically connected with a control button (131) and a interface (14); a button through hole (121) is formed in a front end of the front shell (12); a button panel (11) is mounted in the button through hole (121); the button panel (11) is connected with the control button (131) in a pressing manner; and the interface (14) is arranged in a through hole pre-formed in the inner shell (17) and extends out from the button through hole (121).

6. The ergonomically adaptive adjustment hot compress nursing instrument according to claim 5, wherein the vibration motor (16) is centered at a central axis of the inner shell (17).

\* \* \* \* \*